United States Patent
Williams et al.

(12) 
(10) Patent No.: US 6,964,981 B2
(45) Date of Patent: Nov. 15, 2005

(54) TETRAHYDROFURAN DERIVATIVES AND THEIR USE AS NK-1 ANTAGONISTS

(75) Inventors: Brian John Williams, Great Dunmow (GB); Christopher John Swain, Duxford (GB); Simon Neil Owen, London (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 213 days.

(21) Appl. No.: 10/381,077

(22) PCT Filed: Sep. 10, 2001

(86) PCT No.: PCT/GB01/04038

§ 371 (c)(1),
(2), (4) Date: Mar. 18, 2003

(87) PCT Pub. No.: WO02/24673

PCT Pub. Date: Mar. 28, 2002

(65) Prior Publication Data

US 2003/0199500 A1 Oct. 23, 2003

(30) Foreign Application Priority Data

Sep. 19, 2000 (GB) .............................. 0022988

(51) Int. Cl.$^7$ .................. A61K 31/34; A61P 25/00; C07D 307/20
(52) U.S. Cl. ...................................... 514/473; 549/475
(58) Field of Search ........................... 514/473; 549/475

(56) References Cited

U.S. PATENT DOCUMENTS 5,750,549 A    5/1998   Caldwell et al.

OTHER PUBLICATIONS

Honoo Satake et al, Zoological Science, 20: 533–549, 2003.*
Reichard, G. A. Et Al: "The design and synthesis of novel NK1/NK2 dual antagonists", Bioorganic & Medicinal Chemistry Letters, vol. 10, No. 20, Oct. 16, 2000, pp. 2329–2332.

* cited by examiner

Primary Examiner—Kamal A. Saeed
(74) Attorney, Agent, or Firm—J. Eric Thies; Melvin Winokur

(57) ABSTRACT

The present invention relates compounds that are NK-1 antagonists and that are of use in the treatment or prevention of depression, anxiety, pain, inflammation, migaine, emesis or postherpetic neuralgia.

14 Claims, No Drawings

TETRAHYDROFURAN DERIVATIVES AND THEIR USE AS NK-1 ANTAGONISTS

CROSS REFERENCE TO RELATED APPLICATIONS

This application is a U.S. National Phase application under 35 U.S.C. § 371 of PCT Application No. PCT/GB01/04038, filed Sep. 10, 2001, which claims priority under 35 U.S.C. § 119 from GB Application No. 0022988.0, filed Sep. 19, 2000.

This invention relates to a class of tetrahydrofuran compounds which are useful as tachykinin antagonists. More particularly, the compounds of the invention are useful as neurokinin 1 (NK-1) receptor antagonists.

The present invention provides compounds of the formula (I):

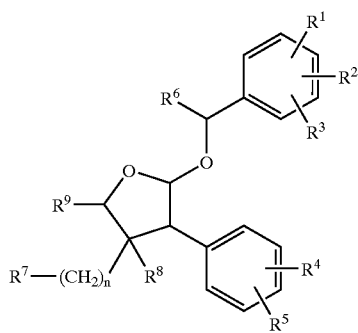

wherein
$R^1$ is hydrogen, halogen, $C_{1-6}$alkyl, $C_{1-6}$alkoxy, fluoro$C_{1-6}$alkyl, fluoro$C_{1-6}$alkoxy, $C_{3-7}$cycloalkyl, $C_{3-7}$cycloalkyl$C_{1-4}$alkyl, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;

$R^2$ is hydrogen, halogen, $C_{1-6}$alkyl, fluoro$C_{1-6}$alkyl or $C_{1-6}$alkoxy substituted by $C_{1-4}$alkoxy;

$R^3$ is hydrogen, halogen or fluoro$C_{1-6}$alkyl;

$R^4$ is hydrogen, halogen, $C_{1-6}$alkyl, $C_{1-6}$alkoxy, fluoro$C_{1-6}$alkyl, fluoro$C_{1-6}$alkoxy, hydroxy, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, fluoro$C_{1-6}$alkyl or $C_{1-6}$alkoxy substituted by $C_{1-4}$alkoxy;

$R^6$ represents hydrogen or a $C_{1-4}$alkyl group optionally substituted by a hydroxy group;

$R^7$ represents halogen, hydroxy, $C_{2-4}$alkenyl, $C_{2-4}$alkynyl, $N_3$, —$NR^{10}R^{11}$, —$NR^aCOR^b$, —$OSO_2R^a$, —$(CH_2)_pNR^a(CH_2)_qCOOR^b$, $COR^a$, $COOR^a$, —N=C=O, or a five membered or six membered nitrogen-containing heteroaromatic ring optionally containing 1, 2 or 3 additional heteroatoms selected from N, O and S which heteroaromatic ring is optionally substituted at any substitutable position by a substituent selected from =O, =S, halogen, hydroxy, —SH, $COR^a$, $CO_2R^a$, -$ZNR^{10}R^{11}$, $C_{1-4}$alkyl, hydroxy$C_{1-4}$alkyl, fluoro$C_{1-4}$alkyl, chloro$C_{1-4}$alkyl, $C_{1-4}$alkoxy, fluoro$C_{1-4}$alkoxy or $C_{1-4}$alkoxy substituted by a $C_{1-4}$alkoxy or hydroxyl group, and wherein said $C_{2-4}$alkenyl and $C_{2-4}$alkynyl groups are optionally substituted by a substituent selected from halogen, hydroxy, $N_3$, —$NR^{10}R^{11}$, —$NR^aCOR^b$, —$OSO_2R^a$, —$(CH_2)_pNR^a(CH_2)_qCOOR^b$, $COR^a$ or $COOR^a$;

or $R^7$ represents a C-linked nitrogen-containing ring of the formula

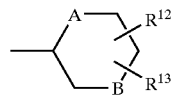

wherein A represents $NR^{14}$ or O, and B represents a bond, $CH_2$, $NR^{14}$ or O, wherein one or both hydrogen atoms in said $CH_2$ moiety may be replaced with one or both of $R^{12}$ and $R^{13}$, or alternatively, one of the hydrogen atoms in said $CH_2$ moiety together with a hydrogen atom from an adjacent carbon are replaced by a double bond;

with the proviso that when A is O, then B is $NR^{14}$;

and with the further proviso that when $R^7$ represents said C-linked nitrogen-containing ring, n is zero and $R^8$ is hydrogen;

$R^8$ represents hydrogen, $C_{1-6}$alkyl, fluoro$C_{1-6}$alkyl, hydroxy, $C_{1-6}$alkoxy or hydroxy$C_{1-6}$alkyl;

$R^9$ represents hydrogen, halogen, $C_{1-6}$alkyl, $CH_2OR^c$, oxo, $CO_2R^a$ or $CONR^aR^b$ where $R^a$ and $R^b$ are as previously defined and $R^c$ represents hydrogen, $C_{1-6}$alkyl or phenyl;

$R^{10}$ is hydrogen, $C_{1-4}$alkyl, $C_{3-7}$cycloalkyl, $C_{3-7}$cycloalkyl$C_{1-4}$alkyl, $C_{2-4}$alkyl substituted by a $C_{1-4}$alkoxy or hydroxyl group, or $R^{10}$ is a five membered or six membered nitrogen-containing heteroaromatic ring as previously defined;

$R^{11}$ is hydrogen or $C_{1-4}$alkyl, $C_{3-7}$cycloalkyl, $C_{3-7}$cycloalkyl$C_{1-4}$alkyl, or $C_{2-4}$alkyl substituted by a $C_{1-4}$alkoxy or hydroxyl group;

or $R^{10}$, $R^{11}$ and the nitrogen atom to which they are attached form a heteroaliphatic ring of 4 to 7 ring atoms, optionally substituted by one or two groups selected from hydroxy, $COR^e$, $CO_2R^e$, $C_{1-4}$alkyl optionally substituted by a $C_{1-4}$alkoxy or hydroxyl group, or $C_{1-4}$alkoxy optionally substituted by a $C_{1-4}$alkoxy or hydroxyl group, or a five membered or six membered nitrogen-containing heteroaromatic ring as previously defined, or said heteroaliphatic ring is substituted by a spiro-fused lactone ring or a spiro-fused ring of the formula —$(CH_2)_rO(CH_2)_s$— (where r and s are each independently zero, 1, 2 or 3 and the sum total of r and s is 3), and said heteroaliphatic ring optionally containing a double bond, which heteroaliphatic ring may optionally contain an oxygen or sulphur ring atom, a group S(O) or $S(O)_2$ or a second nitrogen atom which will be part of a NH or $NR^d$ moiety, where $R^d$ is $C_{1-4}$alkyl optionally substituted by hydroxy or $C_{1-4}$alkoxy, and where $R^e$ is hydrogen, $C_{1-4}$alkyl or benzyl;

or $R^{10}$, $R^{11}$ and the nitrogen atom to which they are attached form a non-aromatic azabicyclic ring system of 6 to 12 ring atoms;

or $R^{10}$, $R^{11}$ and the nitrogen atom to which they are attached form a heteroaliphatic ring of 4 to 7 ring atoms to which is fused a benzene ring or a five membered or six membered nitrogen-containing heteroaromatic ring optionally containing 1, 2 or 3 additional heteroatoms selected from N, O and S;

$R^{12}$ and $R^{13}$ each independently represent hydrogen, hydroxy, $COR^e$, $CO_2R^e$, $C_{1-4}$alkyl optionally substituted by a $C_{1-4}$alkoxy or hydroxyl group, or $C_{1-4}$alkoxy optionally substituted by a $C_{1-4}$alkoxy or hydroxyl group;

or, when they are attached to the same carbon atom, $R^{12}$ and $R^{13}$ may together represent =O, =CHCO$_2R^a$, —$O(CH_2)_mO$—, —$CH_2O(CH_2)_k$—, —$CH_2OCH_2C(O)$—, —$CH_2OCH_2CH(OH)$—, —$CH_2OCH_2C(CH_3)_2$—, —$CH_2OC(CH_3)_2CH_2$—, —$C(CH_3)_2OCH_2CH_2$—, —$CH_2C$ (O)OCH$_2$—, —OC(O)CH$_2$CH$_2$—, —C(O)OCH$_2$CH$_2$—, —C(O)OC(CH$_3$)$_2$CH$_2$—, —C(O)OCH$_2$C(CH$_3$)$_2$—, —OCH$_2$(CH$_2$)$_k$—, —OC(CH$_3$)$_2$CH$_2$CH$_2$—, —OCH$_2$C(CH$_3$)$_2$CH$_2$—, —OCH$_2$CH$_2$C(CH$_3$)$_2$—, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$—, —OCH$_2$CH$_2$C(O)CH$_2$—, or a group of the formula

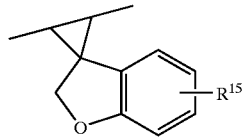

or, where they are attached to adjacent carbon atoms, $R^{12}$ and $R^{13}$ may together represent —OCH$_2$CH$_2$— or —OCH$_2$CH(OH)—, or $R^{12}$ and $R^{13}$ may together form a fused benzene ring;

or, $R^{12}$ and $R^{13}$ together form a C$_{1-2}$alkylene bridge across the pyrrolidine, piperidine, morpholine or piperazine ring to which they are attached;

$R^{14}$ represents hydrogen, benzyl, C$_{1-4}$alkyl, C$_{3-7}$cycloalkyl, C$_{3-7}$cycloalkylC$_{1-4}$alkyl, or C$_{2-4}$alkyl substituted by a C$_{1-4}$alkoxy or hydroxyl group;

$R^{15}$ represents hydrogen, halogen, hydroxy, C$_{1-4}$alkyl, hydroxyC$_{1-4}$alkyl or fluoroC$_{1-4}$alkyl;

Z represents a bond, C$_{1-6}$alkylene or C$_{3-6}$cycloalkylene;

k is 1, 2 or 3;

m is 1 or 2;

n is zero, 1 or 2;

p is 1 or 2; and q is 1 or 2;

and pharmaceutically acceptable salts thereof.

A preferred class of compounds of formula (I) is that wherein $R^1$ is hydrogen, C$_{1-4}$alkyl, C$_{1-4}$alkoxy, halogen or CF$_3$.

Another preferred class of compounds of formula (I) is that wherein $R^2$ is hydrogen, C$_{1-4}$alkyl, C$_{1-4}$alkoxy, halogen or CF$_3$.

Also preferred is the class of compounds of formula (I) wherein $R^3$ is hydrogen, fluorine, chlorine or CF$_3$.

A particularly preferred class of compounds of formula (I) is that wherein $R^1$ is fluorine, chlorine or CF$_3$.

Another particularly preferred class of compounds of formula (I) is that wherein $R^2$ is hydrogen, fluorine, chlorine or CF$_3$.

Also particularly preferred is the class of compounds of formula (I) wherein $R^3$ is hydrogen, fluorine, chlorine or CF$_3$.

Preferably $R^1$ and $R^2$ are in the 3 and 5 positions of the phenyl ring.

More preferably $R^1$ is 3-fluoro or 3-CF$_3$.

More preferably $R^2$ is 5-fluoro or 5-CF$_3$.

More preferably $R^3$ is hydrogen.

Most preferably $R^1$ is 3-F or 3-CF$_3$, $R^2$ is 5-CF$_3$ and $R^3$ is hydrogen.

A further preferred class of compound of formula (I) is that wherein $R^4$ is hydrogen or fluorine, especially hydrogen.

Another preferred class of compounds of formula (I) is that wherein $R^5$ is hydrogen, fluorine, chlorine or CF$_3$.

Preferably $R^4$ is hydrogen or 3-fluoro, especially hydrogen, and $R^5$ is hydrogen or 4-fluoro.

$R^6$ is preferably C$_{1-4}$alkyl optionally substituted by hydroxy. In particular, $R^6$ is preferably a methyl or hydroxymethyl group.

Where —NR$^{10}$R$^{11}$ is defined as a substituent $R^7$ or as a substituent on a heteroaromatic ring in the definition of $R^7$, then $R^{10}$ may aptly be a C$_{1-4}$alkyl group or a C$_{2-4}$alkyl group substituted by a hydroxyl or C$_{1-2}$alkoxy group, $R^{11}$ may aptly be a C$_{1-4}$alkyl group or a C$_{1-2}$alkyl group substituted by a hydroxyl or C$_{1-2}$alkoxy group, or $R^{10}$ and $R^{11}$ may be linked so that, together with the nitrogen atom to which they are attached, they form an azetidinyl, pyrrolidinyl, piperidinyl, morpholino, thiomorpholino, piperazino or piperazino group substituted on the nitrogen atom by a C$_{1-4}$alkyl group or a C$_{2-4}$alkyl group substituted by a hydroxy or C$_{1-2}$alkoxy group. Particularly preferred heteroaliphatic rings formed by —NR$^{10}$R$^{11}$ are azetidine, pyrolidine, piperidine, morpholine, piperazine and N-methylpiperazine, and especially piperidine.

Where the group NR$^{10}$R$^{11}$ represents a heteroaliphatic ring of 4 to 7 ring atoms substituted by two groups, the first substituent is preferably selected from hydroxy, CO$_2$R$^e$ (where R$^e$ is hydrogen, methyl, ethyl or benzyl), or C$_{1-2}$alkyl substituted by hydroxy. The second substituent is preferably a methyl group. Where two substituents are present, said substituents are preferably attached to the same carbon atom of the heteroaliphatic ring.

Where the group NR$^{10}$R$^{11}$ represents a heteroaliphatic ring of 4 to 7 ring atoms substituted by a spiro-fused lactone ring, particularly preferred examples are:

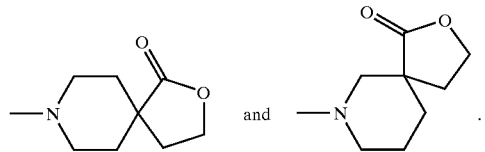

Where the group NR$^{10}$R$^{11}$ represents a heteroaliphatic ring of 4 to 7 ring atoms substituted by a spiro-fused ring of the formula —(CH$_2$)$_r$O(CH$_2$)$_s$—, particularly preferred examples are:

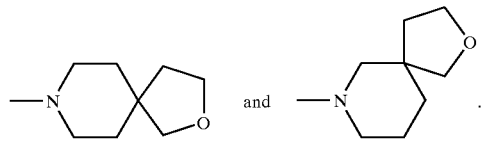

Where the group NR$^{10}$R$^{11}$ represents a heteroaliphatic ring of 4 to 7 ring atoms and said ring contains a double bond, a particularly preferred group is 3-pyrroline.

Where the group NR$^{10}$OR$^{11}$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.3.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where the group NR$^{10}$R$^{11}$ represents a heteroaliphatic ring of 4 to 7 ring atoms to which is fused a benzene ring or a five membered or six membered nitrogen-containing heteroaromatic ring optionally containing 1, 2 or 3 additional heteroatoms selected from N, O and S, said heteroaromatic ring is preferably a five-membered ring, in particular a pyrrole, imidazole or triazole ring, a nitrogen atom of which is preferably included in the heteroaliphatic ring.

Suitable examples of such fused ring systems include

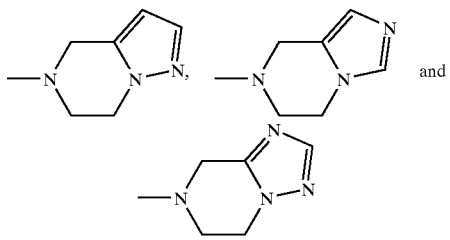

and

Particularly suitable moieties $NR^{10}R^{11}$ include those wherein $NR^{10}R^{11}$ is amino, methylamino, dimethylamino, diethylamino, azetidino, pyrrolidino, piperidino, morpholino and piperazino.

Where $R^7$ represents an optionally substituted five or six-membered nitrogen-containing heteroaromatic ring optionally containing 1, 2 or 3 additional heteroatoms selected from N, O and S, the heteroaromatic ring is selected from pyrrole, pyridine, pyrazole, imidazole, oxazole, isoxazole, thiazole, isothiazole, pyrazine, pyrimidine, pyridazine, triazole, oxadiazole, thiadiazole, triazine, and tetrazole.

Preferred compounds of the present invention are those wherein $R^7$ is a group selected from imidazole, 1,2,3-triazole and 1,2,4-triazole.

Particularly preferred compounds of the present invention are those wherein $R^7$ is a group selected from imidazol-1-yl and 1,2,4-triazol-1-yl.

Where $R^7$ represents an optionally substituted five membered or six membered nitrogen-containing heteroaromatic ring, preferred substituents are $-ZNR^{10}R^{11}$ and $C_{1-2}$alkyl (especially methyl). With reference to the group $ZNR^{10}R^{11}$ defined as a substituent on a heteroaromatic ring in the definition of $R^7$, Z may be a bond or a linear, branched or cyclic group. Favourably Z is a bond or contains 1 to 4 carbon atoms and most favourably 1 to 2 carbon atoms. A particularly favourable group Z is $-CH_2$. In this instance, particularly suitable moieties $NR^{10}R^{11}$ include those wherein $NR^{10}R^{11}$ is amino, methylamino, dimethylamino, diethylamino, azetidino, pyrrolidino, piperidino, morpholino and piperazino. Most especially, $-ZNR^{10}R^{11}$, as a substituent on a heteroaromatic ring in the definition of $R^7$, is preferably $CH_2N(CH_3)_2$.

A further preferred class of compound of formula (I) is that wherein $R^7$ represents halogen (especially iodine), hydroxy, vinyl, $N_3$ or $-OSO_2R^a$ (especially where $R^a$ is methyl).

Another preferred class of compound of formula (I) is that wherein $R^8$ is hydrogen or methyl, and especially hydrogen.

Another preferred class of compounds of formula (I) is that wherein $R^{12}$ is hydrogen, hydroxy, $C_{1-2}$alkyl substituted by hydroxy, $C_{1-4}$alkoxy (especially methoxy) or $CO_2R^e$ (where $R^e$ is hydrogen, methyl ethyl or benzyl).

A further preferred class of compounds of formula (I) is that wherein $R^{13}$ is hydrogen or $C_{1-4}$alkyl (especially methyl).

$R^{12}$ and $R^{13}$ are preferably attached to the same carbon atom. In particular, when B represents $CH_2$, both hydrogen atoms in said $CH_2$ moiety are replaced by $R^{12}$ and $R^{13}$ forming a moiety of the formula $CR^{12}R^{13}$.

Where $R^{12}$ and $R^{13}$ are attached to the same carbon atom they may, in particular, together represent $-C(O)OCH_2CH_2-$.

In a further preferred class of compounds of formula (I), $R^{14}$ preferably represents hydrogen, methyl or ethyl. Where A and B both represent $NR^{14}$, each $R^{14}$ substituent is independently defined.

A further preferred class of compound of formula (I) is that wherein n is 1 or 2, and especially wherein n is 1.

Another preferred class of compound of formula (I) is that wherein $R^9$ is hydrogen.

One favoured group of compounds of the present invention are of the formula (Ia) and pharmaceutically acceptable salts thereof:

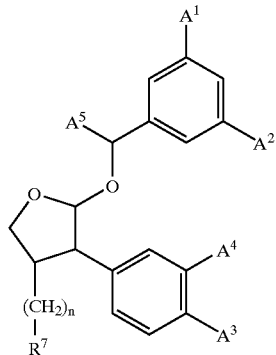

(Ia)

wherein
$A^1$ is fluorine or $CF_3$;
$A^2$ is fluorine or $CF_3$;
$A^3$ is fluorine or hydrogen;
$A^4$ is fluorine or hydrogen, especially hydrogen;
$A^5$ is methyl or hydroxymethyl; and
$R^7$ and n are as defined in relation to formula (I).

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-6}$alkyl" and "fluoro$C_{1-6}$alkoxy" means a $C_{1-6}$alkyl or $C_{1-6}$alkoxy group in which one or more (in particular, 1 to 3) hydrogen atoms have been replaced by fluorine atoms. Similarly, the term "fluoro$C_{1-4}$alkyl" means a $C_{1-4}$alkyl group in which one or more (in particular 1 to 3) hydrogen atoms have been replaced by fluorine atoms. Particularly preferred are fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is propargyl.

When used herein the term "halogen" means fluorine, chlorine, bromine and iodine. The most apt halogens are fluorine and chlorine of which fluorine is preferred, unless otherwise stated.

Specific compounds within the scope of this invention include:

[(2SR, 3SR, 4SR)-2-({(1RS)-1-[3,5-bis(trifluoromethyl) phenyl]-ethyl}oxy)-3-phenyltetrahydro-4-furanyl] methanamine;

[(2SR, 3SR, 4SR)-2-({(1SR)-1-[3,5-bis(trifluoromethyl) phenyl]-ethyl}oxy)-3-phenyltetrahydro-4-furanyl] methanamine;

[(2SR, 3SR, 4SR)-2-({(1SR)-1-[3,5-bis(trifluoromethyl) phenyl]-ethyl}oxy)-3-phenyltetrahydro-4-furanyl]-N,N-dimethylmethanamine;

(2SR, 3SR, 4SR, 2[(1')]RS) 2-(4-aminomethyl-3-phenyl-tetrahydro-furan-2-yloxy)-2-(3,5-bis(trifluoromethyl) phenyl)-ethanol;

(2SR, 3SR, 4SR, 2[(1')]SR) 2-(4-aminomethyl-3-phenyl-tetrahydrofuran-2-yloxy)-2-(3,5-bis(trifluoromethyl) phenyl)-ethanol;

(2RS)-2-[3,5-bis(trifluoromethyl)phenyl]-2-({(2SR,3SR, 4SR)-4-[(N,N-dimethylamino)methyl]-3-phenyltetrahydro-2-furanyl}oxy)ethanol;

[(2RS, 3RS, 4SR)-2-({(1SR)-1-[3,5-bis(trifluoromethyl) phenyl]-ethyl}oxy)-3-phenyltetrahydro-4-furanyl] methanamine;

[(2RS, 3RS, 4SR)-2-({(1RS)-1-[3,5-bis(trifluoromethyl) phenyl]-ethyl}oxy)-3-phenyltetrahydro-4-furanyl] methanamine;

[(2RS, 3RS, 4SR)-5-({(1RS)-1-[3,5-bis(trifluoromethyl) phenyl]-ethyl}oxy)-3-phenyltetrahydro-4-furanyl]-N,N-dimethylmethanamine;

(2RS, 3SR, 4SR, 2[(1')]RS) 2-(4-aminomethyl-3-phenyl-tetrahydrofuran-2-yloxy)-2-(3,5-bis(trifluoromethyl) phenyl)-ethanol;

(2RS, 3SR, 4SR, 2[(1')]SR) 2-(4-aminomethyl-3-phenyl-tetrahydrofuran-2-yloxy)-2-(3,5-bis(trifluoromethyl) phenyl)-ethanol;

and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I) and (Ia) will have the stereochemistry of the 2-, 3-, 4- and 8-positions as shown in formulae (Ib) and (Ic)

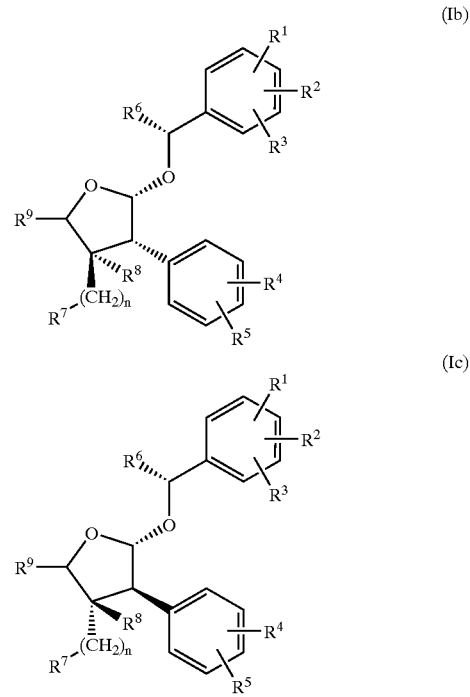

It will be appreciated that the preferred definitions of the various substituents recited herein may be taken alone or in combination and, unless otherwise stated, apply to the generic formula for compounds of the present invention as well as to the preferred classes of compound represented by formula (Ia), formula (Ib) and formula (Ic).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation. Oral compositions such as tablets, pills, capsules or wafers are particularly preferred.

A more detailed description of pharmaceutical compositions that are suitable for the formulation of compounds of the present invention is disclosed in U.S. Pat. No. 6,071,927, the content of which is incorporated herein by reference (see in particular, column 8, line 50 to column 10, line 4).

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. A comprehensive listing of clinical conditions, uses and methods of treatment for which the compounds of the present invention will be useful is disclosed in U.S. Pat. No. 6,071,927, the content of which is incorporated herein by reference (see, in particular, column 10, line 14 to column 22, line 18).

In particular, the compounds of the present invention are useful in the treatment of a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; and anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

The compounds of the present invention are also particularly useful in the treatment of nociception and pain. Diseases and conditions in which pain predominates, include soft tissue and peripheral damage, such as acute trauma, osteoarthritis, rheumatoid arthritis, musculo-skeletal pain, particularly after trauma, spinal pain, myofascial pain syndromes, headache, migraine, episiotomy pain, and burns.

The compounds of the present invention are also particularly useful in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; in the treatment of inflammatory diseases such as inflammatory bowel disease, psoriasis, fibrositis, osteoarthritis, rheumatoid arthritis, pruritis and sunburn; and in the treatment of allergic disorders such as eczema and rhinitis.

The compounds of the present invention are also particularly useful in the treatment of gastrointestinal (GI) disorders, including inflammatory disorders and diseases of the GI tract such as ulcerative colitis, Crohn's disease and irritable bowel syndrome.

The compounds of the present invention are also particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy; by radiation including radiation therapy such as in the treatment of cancer; and in the treatment of post-operative nausea and vomiting.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), compounds of formula (I), in which n is 1, may be prepared by the reaction of a compound of formula (II)

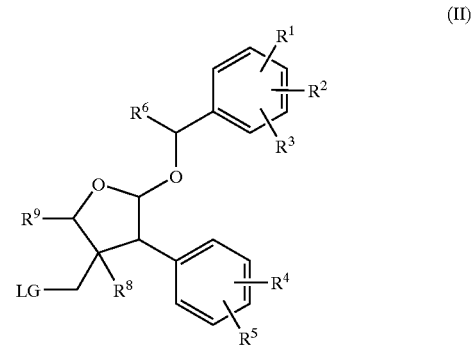

(II)

wherein LG is a suitable leaving group such as an alkyl- or arylsulfonyloxy group (e.g. mesylate or tosylate) or a halogen atom (e.g. bromine, chlorine or iodine); with an appropriate amine of the formula $HNR^{10}R^{11}$, or a heteroaromatic compound suitable for the addition of a five or six-membered nitrogen containing heteroaromatic ring as defined in relation to formula (I), or an azide such as sodium azide.

In each case, the reaction is preferably effected at an elevated temperature, for example, between 40° C. and 80° C., especially between 50° C. and 60° C. The reaction with a heteroaromatic compound is preferably effected in the presence of a suitable organic solvent such as dimethylformamide. The reaction with an azide is preferably effected in the presence of dimethylsulfoxide.

A particularly preferred compound of formula (II) is that wherein the group LG is mesylate—i.e. a compound of formula (I) in which $R^7$ is the group —$OSO_2CH_3$.

According to another general process (B), compounds of formula (I), in which $R^7$ is hydroxy and n is 1 or 2, may be prepared by the interconversion of a corresponding compound of formula (I) in which n is zero and $R^7$ is vinyl, hereinafter referred to as formula (III)

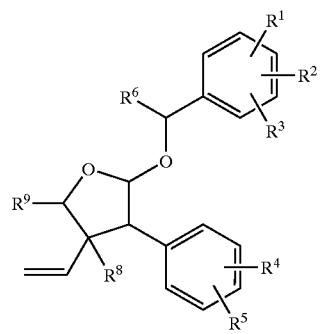

(III)

by reaction with ozone, followed by a reaction with a reducing agent such as sodium borohydride (n is 1), or by reaction with a reducing agent such as borane.tetrahydrofuran complex, followed by hydrogen peroxide in the presence of a base such as sodium hydroxide.

According to another general process (C), compounds of formula (I) may be prepared by the reaction of a compound of formula (IV) with a compound of formula (V)

(IV)

(V)

preferably in the presence of a resin catalyst such as Amberlyst™ 15, and 3 Angstrom molecular sieves.

The reaction is conveniently effected in a suitable solvent such as a halogenated hydrocarbon, for example, dichloromethane, conveniently at room temperature.

According to another general process (D), compounds of formula (I), in which $R^6$ is either methyl or hydroxymethyl, may be prepared by the reaction of a compound of formula (VI)

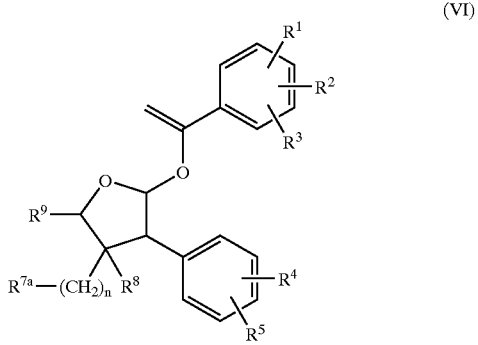

(VI)

wherein $R^{7a}$ is as defined for $R^7$ in relation to formula (I) or, more preferably, is a precursor therefor; under either:

(a) (where $R^6$ is methyl) catalytic hydrogenation conditions (e.g. $H_2$, $Pd(OH)_2$ on carbon) in a suitable solvent such as an ester, for example, ethyl acetate; or (b) (where $R^6$ is hydroxymethyl) reducing conditions (e.g. borane or $BH_3$.THF) followed by treatment with hydrogen peroxide and a base such as sodium hydroxide, conveniently in a solvent such as an ether, for example, tetrahydrofuran.

Where $R^{7a}$ is a precursor group (such as a TBDMS-protected hydroxyl group) deprotection is conveniently effected by treatment with an organic acid such as tetrabutylammonium fluoride.

According to another general process (E), compounds of formula (I) in which $R^7$ is a C-linked nitrogen-containing ring wherein A is $NR^{14}$ and B is $CH_2$ may be prepared by the reaction of a compound of formula (XII)

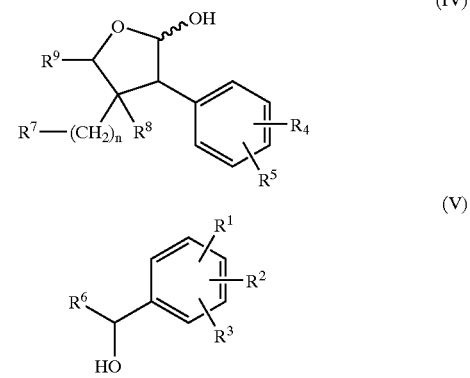

(XII)

in the presence of a suitable catalyst, and if desired reducing the tetrahydropyridinyl moiety, and also if desired removing or replacing the benzyl moiety.

Suitable catalysts of use in this reaction include any catalyst or multicomponent catalyst system that initiates olefin metathesis. Preferred catalysts are single component metal carbene complexes. Particularly preferred catalysts include:

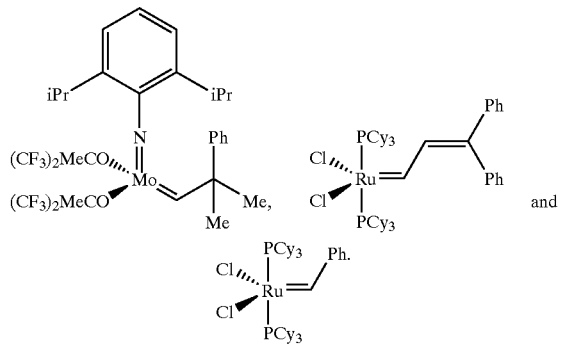

An especially preferred catalyst of use in the present invention is RuCl$_2$(PCy$_3$)$_2$=CHPh, also referred to as Grubbs' catalyst. These catalysts and their use is described, for instance, in the following literature:

Bazan et al., *J. Am. Chem. Soc.*, 1991, 113, 6899 and references cited therein.
Nguyen et al., *J. Am. Chem. Soc.*, 1992, 114, 3974.
Nguyen and Grubbs, *J. Organomet. Chem.*, 1995, 497, 195
Schwab et al., *Angew. Chem. Int. Ed. Eng.*, 1995, 34, 2039.
Schwab et al., *J. Am. Chem. Soc.*, 1996, 118, 100.
Grubbs and Chang, *Tetrahedron*, 1998, 54, 4413.

Suitable organic solvents of use in the reaction include halogenated hydrocarbons, such as dichloromethane or chloroform.

The reaction is conveniently effected at room temperature and pressure, for example at about 20° C.

Reduction of the tetrahydropyridinyl moiety may be effected by conventional methodology, for example, by catalytic hydrogenation in the presence of a suitable catalyst such as palladium on carbon, in a suitable solvent such as an alcohol, for example, methanol. These conditions will also conveniently remove the benzyl moiety (R$^{14}$) which may be replaced using conventional methodology.

According to another general process (F), compounds of formula (I) in which R$^7$ is a C-linked nitrogen-containing ring wherein A is NR$^{14}$ and B is a bond may be prepared by the reaction of a compound of formula (XIII)

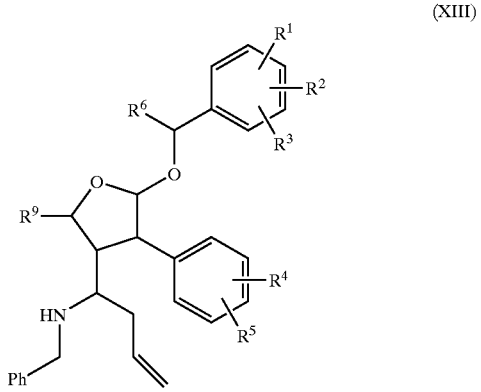

(XIII)

under reducing conditions, for instance, in the presence of borane or borane.tetrahydrofuran complex, followed by treatment with hydrogen peroxide and a base such as sodium hydroxide. The reaction is conveniently effected in a solvent such as an ether, for example, tetrahydrofuran.

If desired, the benzyl moiety (R$^{14}$) may be removed as described above.

According to another general process (G), compounds of formula (I) in which R$^7$ is a C-linked nitrogen-containing ring wherein A is NR$^{14}$ and B is O may be prepared by the reaction of a compound of formula (XIV)

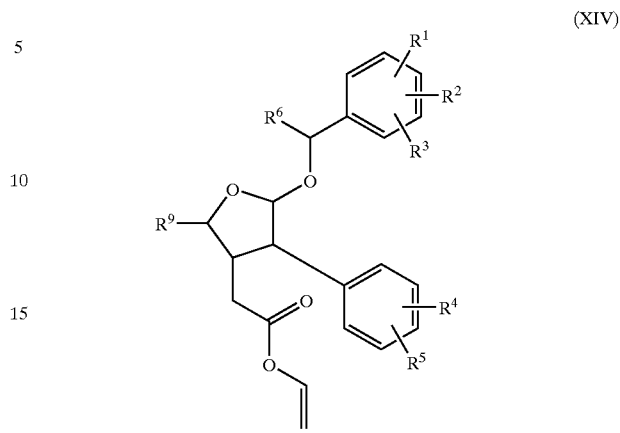

(XIV)

with an amine of the formula R$^{14}$NH$_2$, followed by reduction of the keto function using a suitable reducing agent such as a borohydride, for example sodium cyanoborohydride. The reduction is conveniently effected in a solvent such as an ether, for example, tetrahydrofuran.

According to another general process (H), compounds of formula (I) in which R$^7$ is a C-linked nitrogen-containing ring wherein A is O and B is NR$^{14}$ may be prepared by the reaction of a compound of formula (XV)

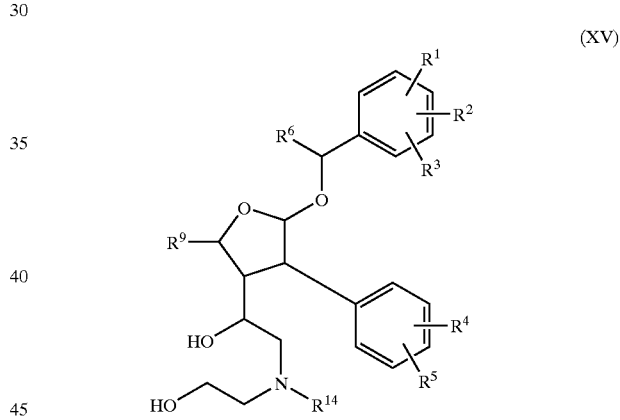

(XV)

under suitable dehydrating conditions, for example, using triphenylphosphine and diethylazodicarboxylate in a suitable solvent such as tetrahydrofuran, at an elevated temperature such as at reflux, or alternatively using methanesulfonyl chloride or benzenesulfonyl chloride in pyridine or triethylamine, in a suitable organic solvent such as dichloromethane, conveniently at a temperature between room temperature and 80° C.

Further details of suitable procedures will be found in the accompanying Examples.

Compounds of formula (II) may be prepared by conventional methods from, for example, a corresponding compound of formula (I) in which R$^7$ is a hydroxyl group. Thus, for example, when LG is a mesylate group a corresponding compound of formula (I) in which R$^7$ is hydroxyl may be reacted with methanesulfonyl chloride in the presence of a base, such as triethylamine. The reaction is conveniently effected in a solvent such as a halogenated hydrocarbon, for example, dichloromethane.

Compounds of formula (III) may be prepared, for example, by the method of general process (C), above Compounds of formula (IV) may be prepared by the reduction of a compound of formula (VII)

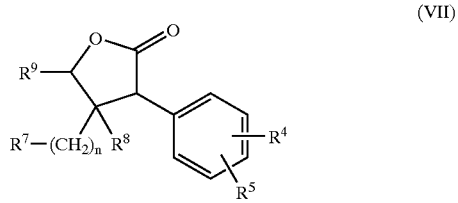
(VII)

using conventional conditions such as sodium borohydride in the presence of a transition metal catalyst such as cerium chloride hexahydrate, in a solvent such as alcohol, for example, ethanol; or using DiBAL in a solvent such as a halogenated hydrocarbon, for example, dichloromethane.

Compounds of formula (VII) in which $R^7$ is vinyl, $R^8$ is hydrogen and n is 1 may be prepared from a compound of formula (VIII)

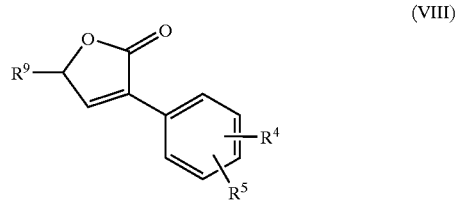
(VIII)

by reaction with a vinyl Grignard reagent such as vinylMgBr, preferably in the presence of copper(I)iodide, and a suitable solvent such as an ether, for example, tetrahydrofuran. This reaction is effected at reduced temperature, for example, below −40° C. and preferably at −78° C.

Compounds of formula (VI) may be prepared by the reaction of a compound of formula (X)

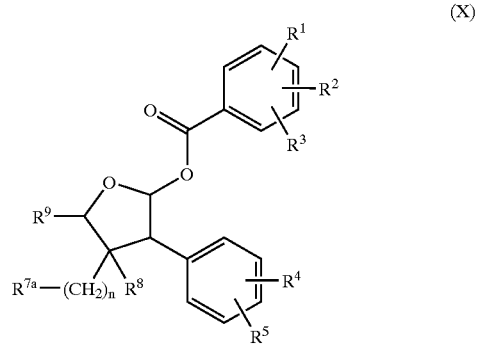
(X)

with dimethyltitanocene in a solvent such as toluene, pyridine or tetrahydrofuran, or a mixture thereof.

Compounds of formula (X) may be prepared by the reaction of a compound of formula (VII) with L-Selectride™ (lithium tri-sec-butylborohydride) followed by treatment with a compound of formula (XI)

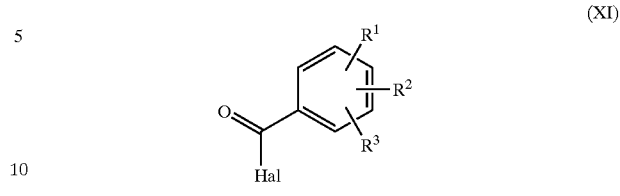
(XI)

wherein Hal is a halogen atom, preferably chlorine.

Compounds of formula (XII) may be prepared from a compound of formula (XIII) above, by N-alkylation with an allyl halide, for example, allyl bromide. The reaction is preferably effected in the presence of an inorganic base such as potassium carbonate and a suitable solvent such a dimethylformamide. The reaction is conveniently effected at a temperature between room temperature and 100° C.

Compounds of formula (XIII) may be prepared from a compound of formula (XVI)

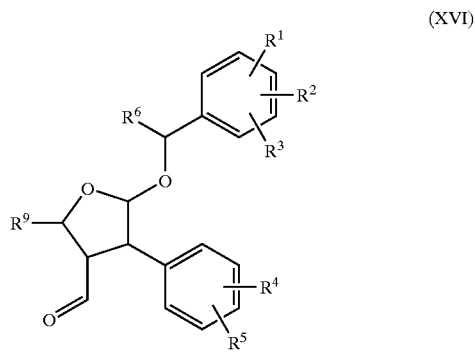
(XVI)

by reaction with benzylamine in a suitable solvent such as a halogenated hydrocarbon, for example, dichloromethane. Following basification, using for example basic alumina, the reaction mixture is filtered, evaporated and the residue dissolved in a suitable solvent such as an ether, for example, tetrahydrofuran. Reaction with a suitable alkylating reagent such as a Grignard reagent, for example, allyl magnesium bromide, in the presence of a suitable solvent such as an ether, for example, diethyl ether, affords the compound of formula (XIII).

Compounds of formula (XVI) may be prepared from a compound of formula (III) by an ozonolysis reaction, using ozone at a low temperature, for example, between −60° C. and −100° C., in a suitable solvent such as a halogenated hydrocarbon, for example, dichloromethane, or an alcohol, for example, methanol, or a mixture thereof. The intermediate ozonide thus formed need not be isolated but instead is decomposed using a suitable reducing agent, for example, dimethyl sulfide, trimethyl phosphite or thiourea.

Compounds of formula (XIV) may be prepared from a compound of formula (XVII)

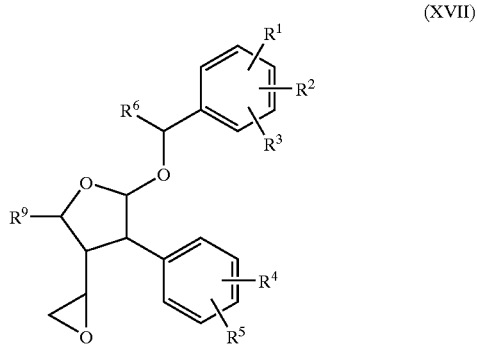

(XVII)

by reaction with allyl alcohol in the presence of a suitable reducing reagent, such as a hydride, for example sodium hydride, in a suitable solvent such as an ether, for example tetrahydrofuran, at an elevated temperature, for example, between 60° C. and 100° C., followed in a second step by an oxidation reaction, for example using a mild oxidizing reagent such as Dess-Martin periodinane, in a suitable solvent such as a halogenated hydrocarbon, for example dichloromethane, conveniently at room temperature.

Compounds of formula (XVII) may be prepared from a compound of formula (III) by an epoxidization reaction using a peracid, for example, m-chloroperbenzoic acid. The reaction is effected in a solvent such as a halogenated hydrocarbon, for example, dichloromethane, conveniently at room temperature.

Compounds of formula (XV) may be prepared from a compound of formula (XVII) by reaction with a suitable amine of the formula $R^{14}NHCH_2CH_2OH$. The reaction is conveniently effected in a solvent such as an alcohol, for example methanol, at an elevated temperature, for example at the reflux temperature of the solvent.

Compounds of formula (V), (VIII) and (XI) are either known compounds or may be prepared by methods analogous to those described herein.

It will be appreciated that the general methodology described above may be adapted, using methods that are readily apparent to one of ordinary skill in the art, in order to prepare further compounds of the present invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 100 nM on said test method.

The following non-limiting Examples serve to illustrate the preparation of compounds of the present invention:

DESCRIPTION 1
3-Iodo-3-phenyl-prop-2-en-1-ol

Red-Al™ (3.4M in toluene, 33 ml) was dissolved in diethyl ether (100 ml) and cooled to −10° C. to which 3-phenyl-2-propyn-1-ol (10 g, 0.076 mol) dissolved in diethyl ether (10 ml) was added dropwise, causing the solution to turn a dark red/brown colour. The reaction was stirred for 1 hour. The solution was cooled to −78° C. and iodine monochloride (1.0M solution in dichloromethane, 114 ml) was added causing the solution to turn a dark brown colour. The mixture was allowed to warm to room temperature and stirred for 1 hour. A 10% solution of potassium sodium tartaric acid (800 ml) was added, producing a white precipitate, this was removed by filtration and the filtrate was extracted with diethyl ether (3×75 ml). The combined organic extracts were washed with sodium thiosulphate (5×60 ml), brine, dried ($MgSO_4$) and the solvent removed in vacuo to afford the crude title compound as a light brown oil (19.5 g, 95%).

$^1H$ NMR (250 MHz, $CDCl_3$) δ 1.76 (1H, t, J 5.7 Hz), 4.39 (2H, t, J 5.6 Hz), 6.25 (1H, t, J 5.8 Hz), 7.10–7.50 (5H, m).

DESCRIPTION 2
3-phenyl-5H-furan-2-one

3-Iodo-3-phenyl-prop-2-en-1-ol (Description 1; 1 g, 3.8 mM) was dissolved in tetrahydrofuran (20 ml) and Hunig's base (2.67 ml, 15.4 mM) and degassed using a Firestone valve (×3). Carbon monoxide was bubbled through the solution for 10 minutes after which tris(dibenzylideneacetone)dipalladium (141 mg; 4 mol %) and 1,4 bis(diphenylphosphino) butane (65 mg; 4 mol %) were added. The reaction was heated at 50° C. under an atmosphere of carbon monoxide. After 2 hours, when the reaction was 50% complete, an extra addition of the palladium source and phosphine ligand were made. After a further 2 hours the reaction was cooled, filtered, the solvent removed in vacuo and the residue was dispersed between ethyl acetate and water. The aqueous layer was extracted with ethyl acetate (2×40 ml), the combined organic layers were washed with brine, dried over $MgSO_4$ and the solvent removed in vacuo. Purification was carried out by silica chromatography eluting in increasing concentrations of ethyl acetate in hexane (0–15%) to afford the title compound as a tan-coloured solid (0.56 g, yield 91%).

DESCRIPTION 3
5-Oxo-4-phenyl-tetrahydrofuran-3-carbonitrile

3-Phenyl-5H-furan-2-one (Description 2; 4.5 g, 0.028 mol), and acetone cyanohydrin (3.06 ml) were dissolved in $CH_3CN$ (80 ml) and cooled to −0° C. Tetramethylguanidine (3.5 ml) was added dropwise over 15 minutes and the reaction left to stand for a further 15 minutes. 0.5M HCl (100 ml) was added and the reaction mixture de-colourised and the product extracted with ethyl acetate (2×40 ml), washed with brine (2×30 ml) and dried over $MgSO_4$. The solvent was removed in vacuo to afford a brown oil which was a mixture of the cis and trans isomers. Purification was carried out using flash column chromatography on silica gel eluting in increasing concentrations of ethyl acetate in hexane (0–60%) to yield the title compound (2.93 g, 56%). The only isolated product from the column was the more thermodynamically stable trans isomer.

$^1$H-NMR (250 MHz, $CDCl_3$) δ trans isomer: 3.54 (1H, ddd, J 10.9 Hz, 9.6 Hz, 8.1 Hz), 4.10 (1H, d, J 11.0 Hz), 4.43 (1H, t, J 9.4 Hz), 4.69 (1H, t, J 9.2 Hz), 7.40 (5H, m).

$^1$H-NMR (250 MHz, $CDCl_3$) δ cis isomer: 3.87 (1H, m), 4.10 (1H, d, J 2.3 Hz), 4.56 (2H, d, J 6.0 Hz), 7.41 (5H, m).

DESCRIPTION 4
(5-Oxo-4-phenyl-tetrahydrofuran-3-ylmethyl)carbamic acid tert-butyl ester 5-Oxo-4-phenyl-tetrahydrofuran-3-carbonitrile (Description 3; 7.1 g, 0.038 mol) was added to di-tert-butyldicarbonate (24 g), platinum dioxide catalyst (1.4 g), ethyl acetate (150 ml) and acetic acid (20 ml) and shaken under an atmosphere of hydrogen (50 psi) for 24 hours. The catalyst was removed by filtration, solvent removed in vacuo and the residue was purified using flash column chromatography on silica gel eluting in increasing concentrations of ethyl acetate in hexane (5–50%) to give the title compound as a brown oil (2.16 g).

DESCRIPTION 5

(3RS, 4RS) 4-Aminomethyl-3-phenyl-dihydrofuran-2-one (5-Oxo-4-phenyl-tetrahydrofuran-3-ylmethyl)carbamic acid tert-butyl ester (Description 4; 2.16 g, 7.4 mmol) was dissolved in dichloromethane (10 ml), cooled to 0° C., trifluoroacetic acid (1 ml) was added and the reaction was left to stand for 20 minutes to warm to room temperature. TLC showed the reaction to be incomplete so extra trifluoroacetic acid (1 ml) was added and the reaction was left for a further 30 minutes. The solvent was removed in vacuo and the residue was dispersed between ethyl acetate and saturate potassium carbonate solution. The aqueous layer was extracted with ethyl acetate (2×30 ml), the combined organic layers were washed with brine, dried over MgSO$_4$, filtered and evaporated to dryness. Purification was carried out by flash column chromatography on silica gel eluting in increasing concentrations of methanol in dichloromethane and 0.2% ammonia (1–10%) to afford the title compound (2.15 g).

m/z (ES$^+$) 191 (M+H, 100%).

DESCRIPTION 6

(3RS, 4RS) 4-[(N,N-Dibenzylamino)-methyl]-3-phenyl-dihydrofuran-2-one (3RS, 4RS) 4-Aminomethyl-3-phenyl-dihydrofuran-2-one (2.15 g, 0.011 mol) was added to potassium carbonate (15.5 g), benzyl bromide (6.69 ml) and dimethylformamide (10 ml) and stirred for 3 hours at 50° C. dimethylformamide was removed in vacuo and the reaction was dispersed between ethyl acetate (40 ml) and water (60 ml), the aqueous phase was washed with ethyl acetate (2×30 ml) and the organic layers were combined and washed with brine solution (100 ml) and dried over MgSO$_4$. The solvent was removed in vacuo and purified by flash column chromatography on silica gel and eluting in increasing concentrations of ethyl aceate in hexane (5–50%) to give the title compound (1.15 g, 46%).

$^1$H-NMR (250 MHz, CDCl$_3$) δ 2.57 (2H, dd, J 6.1 Hz, 2.7 Hz), 2.86 (1H, m), 3.20 (1H, d, J 13.5 Hz), 3.35 (2H, d, J 13.4 Hz), 3.63 (2H, d, J 13.3 Hz), 3.83 (1H, t, J 8.9 Hz), 4.55 (1H, t, J 7.6 Hz). m/z (ES$^+$) 371 (M+H, 100%).

DESCRIPTION 7

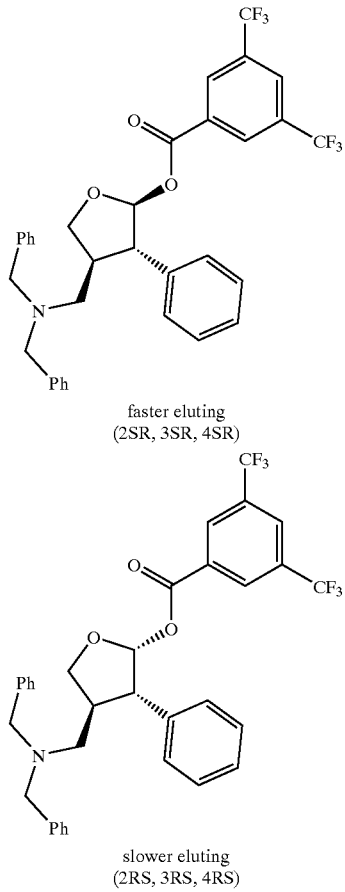

faster eluting
(2SR, 3SR, 4SR)

slower eluting
(2RS, 3RS, 4RS)

(a) (2SR, 3SR, 4SR) 3,5-Bis(trifluoromethyl)benzoic acid 4-[(N,N-dibenzylamino)methyl]-3-phenyl-tetrahydrofuran-2-yl ester; and
(b) (2RS, 3SR, 4SR) 3,5-Bis(trifluoromethyl)benzoic acid 4-[(N,N-dibenzylamino)methyl]-3-phenyl-tetrahydrofuran-2-yl ester (3RS, 4RS) 4-[N,N-Dibenzylamino)-methyl]-3-phenyl-dihydrofuran-2-one (Description 6; 1.53 g, 4 mmol) was dissolved in tetrahydrofuran (15 ml) under an atmosphere of nitrogen and cooled to −78° C. L-Selectride™ (8.25 ml) was added dropwise and the reaction was left to stand for 30 minutes. Further L-Selectride™ (1.65 ml) was added, 3,5-bis-trifluoromethyl-benzoyl chloride (1.86 ml) was added dropwise and the solution was left to stand for 16 hours at −78° C. Further 3,5-bis-trifluoromethyl-benzoyl chloride (0.372 ml) was added and the reaction was warmed to room temperature for 20 minutes. The reaction was then quenched with saturated sodium carbonate (400 ml), dispersed between ethyl acetate (100 ml) and the aqueous layers washed with ethyl acetate (3×50 ml). The organic extracts were combined and dried over MgSO$_4$. The solvent was removed in vacuo and purified by flash column chromatography on silica gel and eluting in increasing concentrations of ethyl acetate in hexane (0–20%) to yield the title compounds.

Faster eluting isomer (a) (2SR, 3SR, 4SR) (0.8 g, yield 32%).

$^1$H-NMR (360 MHz, CDCl$_3$) δ 2.40–2.56 (1H, m), 2.61 (1H, dd, J 8.9 Hz, 2.4 Hz), 3.14 (2H, br s), 3.43 (2H, d, J 13.4 Hz), 3.67 (2H, d, J 13.4 Hz), 3.71 (1H, t, J 8.0 Hz), 4.47 (1H, t, J 7.9 Hz), 6.38 (1H, d, J 4.1 Hz), 7.21–7.33 (15H, m), 7.98 (1H, s), 8.17 (2H, s).

Slower eluting isomer (b) (2RS, 3SR, 4SR) (0.32 g, yield 13%).

¹H-NMR (360 MHz, CDCl₃) δ 2.63 (1H, d, J 8.4 Hz), 2.65 (1H, d, J 4.8 Hz), 2.78 (1H, m), 3.22 (1H, dd, J 4.1 Hz, 2.0 Hz), 3.48 (4H, dd, J 26 Hz, 13.5 Hz), 3.83 (1H, t, J 8.5 Hz), 4.47 (1H, t, J 8.4 Hz), 6.34 (1H, d, J 2.2 Hz), 7.10–7.38 (15H, m), 8.06 (1H, s), 8.30 (2H, s).

DESCRIPTION 8

(2SR, 3SR, 4SR) N,N-Dibenzyl-{5-[1-(3,5-bis(trifluoromethyl)-phenyl)vinyloxy]-4-phenyl-tetrahydrofuran-3-ylmethyl}amine (2SR, 3SR, 4SR) 3,5-Bis(trifluoromethyl)benzoic acid 4-[(N,N-dibenzylamino)methyl]-3-phenyl-tetrahydrofuran-2-yl ester (Description 7(a); 1.03 g, 1.7 mmol) was azeotroped with tetrahydrofuran (2×10 ml), dissolved in tetrahydrofuran (15 ml) and degassed with Firestone™ valve (×3). Bis(cyclopentadiene) titanium dimethyl (1.8 ml, 2.8M in toluene) was added and the mixture was heated to 60° C. in the dark. Further bis(cyclopentadiene) titanium dimethyl (1 ml) was added and the reaction was left to stand for 18 hours. The reaction was quenched with a slurry of sodium carbonate (4 g), water (2.5 ml) and methanol (50 ml), which caused it to turn yellow, and the reaction was left to stand at 40° C. for 16 hours under nitrogen. The solid was removed by filtration and the solvent removed in vacuo to afford a yellow solid. The solid was dispersed between water (50 ml) and ethyl acetate (40 ml), the aqueous layer was washed with ethyl acetate (3×20 ml) and brine (1×50 ml), and dried over MgSO₄. The solvent was removed in vacuo and the product purified by flash column chromatography on silica gel and eluting in increasing concentrations of dichloromethane in hexane (10–100%) to give the title compound (299 mg, yield 29%).

¹H-NMR (360 MHz, CDCl₃) δ 3.14 (1H, dd, J 4.7 Hz, 2.3 Hz), 3.37 (2H, dd, J 22.4 Hz, 13.5 Hz), 3.49 (1H, m), 3.59 (2H, d, J 13.6 Hz), 3.76 (2H, d, J 13.5 Hz), 3.75 (1H, t, J 8.8 Hz), 4.40 (1H, t, J 2.3 Hz), 4.62 (1H d, J 3.2 Hz), 4.84 (1H, d, J 3.1 Hz), 6.69 (1H, d, J 1.4 Hz), 7.11–7.37 (15H, m), 7.78 (1H, s), 7.88 (1H, s). m/z (ES⁺) 611 (M+H, 44%).

DESCRIPTION 9

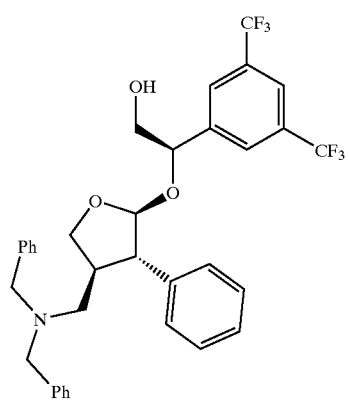

slower eluting
(2SR, 3SR, 4SR, 2[(1')]RS)

-continued

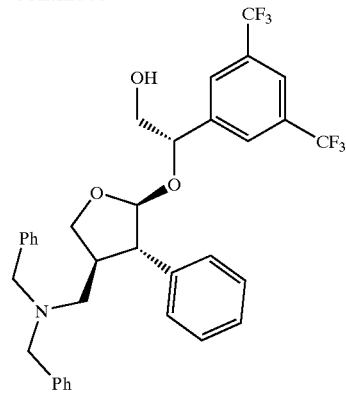

faster eluting
(2SR, 3SR, 4SR, 2[(1')]SR)

(a) (2SR, 3SR, 4SR, 2[(1')]SR) 2-(3,5-Bis(trifluoromethyl)phenyl)-2-{4-[(N,N-dibenzylamino)methyl]-3-phenyl-tetrahydrofuran-2-yloxy}-ethanol; and (b) (2SR, 3SR, 4R, 2[(1')]RS) 2-(3,5-Bis(trifluoromethyl)phenyl)-2-{4-[(N,N-dibenzylamino)methyl]-3-phenyl-tetrahydrofuran-2-yloxy}-ethanol (2SR, 3SR, 4SR) Dibenzyl-{5-[1-(3,5-bis(trifluoromethyl)phenyl)vinyloxy]-4-phenyl-tetrahydrofuran-3-ylmethyl}amine (Description 8; 299 mg, 49 mmol) was azeotroped in tetrahydrofuran (3×1 ml), dissolved in tetrahydrofuran (10 ml) and cooled to −10° C. Borane-THF (1.47 ml, 1.0M in THF) was added dropwise and the reaction left to stand for 6 hours at room temperature. The mixture was quenched with a solution of sodium hydroxide (1.85 ml, 2M) and hydrogen peroxide (30 ml) at −10° C. and left to stand for 45 minutes. The mixture was then dispersed between ethyl acetate (20 ml) and water (40 ml) and the water layer was washed with ethyl acetate (2×15 ml). The organic extracts were combined and washed with brine (1×30 ml) and dried over MgSO₄. The solvent was removed in vacuo and the residue purified by flash column chromatography on silica gel and eluting in increasing concentrations of ethyl acetate in hexane (2.5–50%) to give the title compounds.

Slower eluting isomer (a) (2SR, 3SR, 4SR, 2[(1')]RS) (53 mg, yield 17%).

¹H-NMR (360 MHz, CDCl₃) δ 2.59 (1H, d, J 7.5 Hz), 2.63–2.66 (1H, m), 2.71 (1H, d, J 7.3 Hz), 2.99 (1H, dd, J 7.0 Hz, 3.0 Hz), 3.38 (1H, d, J 13.4 Hz), 3.41–3.47 (1H, m), 3.53 (2H, d, J 13.1 Hz), 3.58 (2H, d, J 13.5 Hz), 3.74 (1H, t, J 8.4 Hz), 4.36 (1H, t, J 7.6 Hz), 4.68 (1H, dd, J 7.5 Hz, 3.1 Hz), 4.86 (1H, d, J 3.0 Hz), 7.01–7.32 (15H, m), 7.59 (2H, s), 7.72 (1H, s).

Faster eluting isomer (b) (2SR, 3SR, 4SR, 2[(1')]SR) (33 mg, yield 11%).

¹H-NMR (360 MHz, CDCl₃) δ 1.78 (1H, br d), 2.42 (1H, dd, J 12.1 Hz, 7.2 Hz), 2.56–2.61 (1H, m), 2.70 (1H, dd, J 12.1 Hz, 7.5 Hz), 3.10 (1H, dd, J 6.1 Hz, 2.3 Hz), 3.25 (1H, t, J 8.4 Hz), 3.41 (2H, d, J 13.4 Hz), 3.38–3.46 (1H, m), 3.52 (2H, d, J 13.4 Hz), 3.47–3.55 (1H, m), 4.09 (1H, t, J 8.1 Hz), 4.54 (1H, dd, J 7.5 Hz, 3.7 Hz), 5.15 (1H, d, J 2.4 Hz), 7.18–7.35 (15H, m), 7.63 (2H, s), 7.78 (1H, s).

DESCRIPTION 10

(2RS, 3SR, 4SR) N,N-Dibenzyl-{5-[1-(3,5-bis(trifluoromethyl)-phenyl)vinyloxy]-4-phenyl-tetrahydrofuran-3-ylmethyl}amine (2RS, 3SR, 4SR) 3,5-Bis(trifluoromethyl)benzoic acid 4-[(N,N-dibenzylamino)methyl]-3-phenyl-tetrahydrofuran- 2-yl ester (Description 7(b); 0.64 g) was used treated according to the procedure described in Description 8. Purification was carried out by flash column chromatography on silica gel and eluting in increasing concentrations of ethyl acetate in hexane (0–10%) to give the title compound (0.32 g, 50%). m/z 612 (M+H, 100).

DESCRIPTION 11

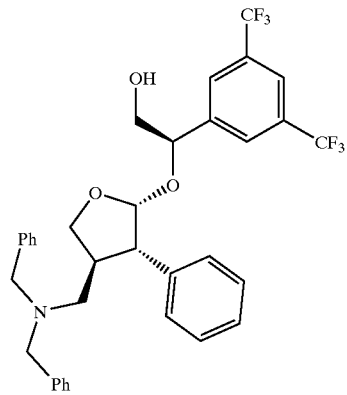

faster eluting
(2RS, 3SR, 4SR, 2[(1')]RS)

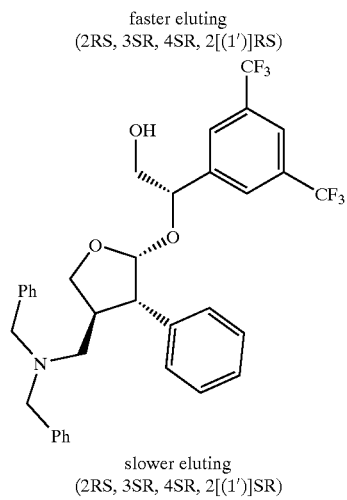

slower eluting
(2RS, 3SR, 4SR, 2[(1')]SR)

(a) (2RS, 3SR, 4SR, 2[(1')]RS) 2-(3,5-Bis(trifluoromethyl)phenyl)-2-{4-[(N,N-dibenzylamino)methyl]-3-phenyl-tetrahydrofuran-2-yloxy}-ethanol; and
(b) (2RS, 3SR, 4SR, 2[(1')]SR) 2-(3,5-Bis(trifluoromethyl)phenyl)-2-{4-[(N,N-dibenzylamino)methyl]-3-phenyl-tetrahydrofuran-2-yloxy}-ethanol (2RS, 3SR, 4SR) N,N-Dibenzyl-{5-[1-(3,5-bis(trifluoromethyl)phenyl)-vinyloxy]-4-phenyl-tetrahydrofuran-3-ylmethyl}amine (Description 10; 0.129 g) was hydroborated using the method described in Description 9. Purification was carried out by flash silica chromatography eluting with increasing concentrations of ethyl acetate (0–20%) in hexane.

Faster eluting isomer (a) (2RS, 3SR, 4SR, 2[(1')]RS) (23.7 mg, yield 18%).

$^1$H-NMR (360 MHz, CDCl$_3$) δ 1.21(1H, dd, J 9.7 Hz, 4.0 Hz), 2.41(1H, dd, J 12.7 Hz, 9.7 Hz), 2.53 (1H, dd, J 12.7 Hz, 4.7 Hz), 2.90 (1H, dd, J 11.2 Hz, 4.6 Hz), 3.12–3.28 (1H, m), 3.30–3.52 (5H, m), 3.64 (2H, d, J 13.4 Hz), 4.12 (11H, t, J 8.5 Hz), 4.50 (1H, dd, J 8.0 Hz, 3.5 Hz), 5.11 (1H, d, J 4.7 Hz), 7.10–7.44 (15H, m), 7.71 (2H, s), 7.79 (1H, s).

Slower eluting isomer (b) (2RS, 3SR, 4SR, 2[(1')]SR) (37 mg, yield 28%).

$^1$H-NMR (360 MHz, CDCl$_3$) δ 2.43 (1H, dd, J 12.7 Hz, 9.9 Hz), 2.53(1H, 12.7 Hz, 4.6 Hz), 2.85(1H, dd, J 11.3 Hz, 4.8 Hz), 3.01 (1H, dd, J 9.1 Hz, 3.6 Hz), 3.11–3.24 (1H, m), 3.37 (2H, d, J 13.5 Hz), 3.48–3.74 (5H, m), 4.42 (1H, t, J 8.4 Hz), 4.69 (1H, dd, J 7.6 Hz, 3.0 Hz), 4.92(11, d, J 4.8 Hz), 7.16–7.20 (17H, m), 7.66 (1H, s).

EXAMPLE 1

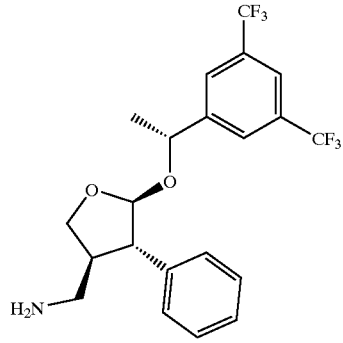

faster eluting
(2SR, 3SR, 4SR, 2[(1')]RS)

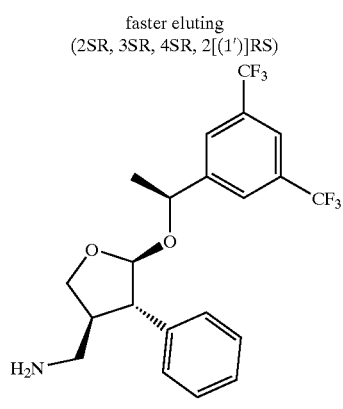

slower eluting
(2SR, 3SR, 4SR, 2[(1')]SR)

(a) [(2SR, 3SR, 4SR)-2-({(1RS)-1-[3,5-Bis(trifluoromethyl)phenyl]-ethyl}oxy)-3-phenyltetrahydro-4-furanyl]methanamine; and
(b) [(2SR, 3SR, 4SR)-2-({(1SR)-1-[3,5-Bis(trifluoromethyl)phenyl]-ethyl}oxy)-3-phenyltetrahydro-4-furanyl]methanamine (2SR, 3SR, 4SR) N,N-Dibenzyl-{5-[1-(3,5-bis(trifluoromethyl)phenyl)-vinyloxy]-4-phenyl-tetrahydrofuran-3-ylmethyl}amine (Description 8; 0.25 g) was dissolved in methanol (20 ml), ammonium formate (130 mg) was added and the mixture degassed with nitrogen for 10 minutes. 10% palladium on carbon (80 mg) was added heated at reflux for 3 hours. The reaction was filtered and evaporated to dryness in vacuo and purification was carried out by flash chromatography elution in increasing concentrations (0–2%) methanol in dichloromethane with 0.2% ammonia.

Faster eluting isomer (a) (2SR, 3SR, 4SR, 2[(1')RS]) (43 mg, yield 24%).

$^1$H-NMR (250 MHz, CDCl$_3$) δ 1.40 (3H, d, J 6.6 Hz), 2.29–2.47 (1H, m), 2.80 (1H, dd, J 12.5 Hz, 7.8 Hz), 2.95 (1H, dd, J 12.5 Hz, 6.1 Hz), 3.11 (1H, dd, J 7.0 Hz, 2.4 Hz), 3.58 (1H, t, J 8.7 Hz), 4.16 (1H, t, J 8.1 Hz), 4.80 (1H, q, J 6.5 Hz), 5.25 (1H, d, J 2.4 Hz), 7.18–7.41 (5H, m), 7.77 (2H, s), 7.80 (1H, s).

m/z (ES$^+$) 434 (H+1, 4%), 176 (M−273, 100%).

Slower eluting isomer (b) (2SR, 3SR, 4SR, 2[(1')SR]) (35 mg, yield 20%).

¹H-NMR (360 MHz, CDCl₃) δ 1.48 (3H, d, J 6.6 Hz), 2.38–2.49 (1H, m), 2.84 (1H, dd, J 12.5 Hz, 7.9 Hz), 2.97 (1H, dd, J 12.4 Hz, 5.8 Hz), 3.07 (1H, dd, J 7.5 Hz, 3.1 Hz), 3.90 (1H, t, J 8.7 Hz), 4.32 (1H, t, J 8.0 Hz), 4.81 (1H, d, J 3.1 Hz), 4.90 (1H, q, J 6.6 Hz), 7.14–7.36 (5H, m), 7.63 (2H, s), 7.74 (1H, s).
m/z (ES⁺) 434 (H+1, 50%), 176 (M−273, 100%).

EXAMPLE 2
[(2SR, 3SR, 4SR)-2-({(1SR)-1-[3,5-Bis(trifluoromethyl) phenyl]-ethyl}oxy)-3-phenyltetrahydro-4-furanyl]-N,N-dimethylmethanamine

[(2SR, 3SR, 4SR)-2-({(1SR)-1-[3,5-Bis(trifluoromethyl) phenyl]ethyl}oxy)-3-phenyltetrahydro-4-furanyl] methanamine (Example 1(b); 52 mg), was dissolved in isopropanol (30 ml) and one equivalent of etheral HCl was added. The reaction mixture was degassed with nitrogen before the addition of formaldehyde (37% in water, 0.25 ml) and 10% palladium on carbon (15 mg). The reaction was shaken under 50 psi of hydrogen for 3 hours. The solvent was removed in vacuo and the residue was dispersed between ethyl acetate and saturated potassium carbonate solution. The aqueous layer was extracted with ethyl acetate (2×25 ml), the combined organic extracts were washed with brine, dried over MgSO₄, filtered and solvent removed in vacuo. Purification was carried out by preparative TLC eluting with 5% methanol in ethyl acetate with 0.2% ammonia to give the title compound (17 mg, yield 31%).

¹H-NMR (360 MHz, CDCl₃) δ 1.48 (3H, d, J 6.6 Hz), 2.19 (6H, s), 2.42–2.58 (3H, m), 3.05 (1H, dd, J 6.4 Hz, 2.8 Hz), 3.90 (1H, t, J 8.1 Hz), 4.33 (1H, dd, J 8.7 Hz, 6.6 Hz), 4.80 (1H, d, J 2.9 Hz), 4.90 (1H, q, J 6.6 Hz), 7.12–7.31 (5H, m), 7.64 (2H, s), 7.69 (1H, s). m/z (ES⁺) 462 (H+1, 100%).

EXAMPLE 3
(2SR, 3SR, 4SR, 2[(1')]RS) 2-(4-Aminomethyl-3-phenyl-tetrahydro-furan-2-yloxy)-2-(3,5-bis(trifluoromethyl) phenyl)-ethanol (2SR, 3SR, 4SR, 2[(1')]SR) 2-(3,5-Bis(trifluoromethyl) phenyl)-2-{4-[(N,N-dibenzylamino)methyl]-3-phenyl-tetrahydrofuran-2-yloxy}-ethanol (Description 9(a); 53 mg, 0.084 mmol) was dissolved in methanol (5 ml) and paladium on carbon (10 mg) and ammonium formate (37.1 mg) were added and the mixture refluxed for 1 hour. Further ammonium formate (20 mg) was added and the mixture refluxed for another hour. The catalyst was filtered off, the solvent was removed in vacuo and the residue purified using preparative TLC plates in 6% methanol in dichloromethane and 0.2% ammonia. The product was removed from the silica by washing with methanol (2×20 ml) and the solvent removed in vacuo. The residue was dissolved in dichloromethane (10 ml) and dried over MgSO₄ to give the title compound (20.2 mg, 54%).

¹H-NMR (360 MHz, CDCl₃) δ 2.52–2.54 (1H, m), 2.8–3.05 (2H, m), 3.17 (1H, d, J 4.4 Hz), 3.69 (2H, d, J 5.0 Hz), 4.07 (1H, t, J 8.6 Hz), 4.35 (1H, t, J 8.3 Hz), 4.89 (1H, t, J 5.7 Hz), 4.97 (1H, d, J 2.5 Hz), 7.16–7.35 (5H, m), 7.70 (2H, s), 7.74 (1H, s). m/z (ES⁺) 450 (M+H, 3%), 176 (M−273, 100%).

EXAMPLE 4
(2SR, 3SR, 4SR, 2[(1')]SR) 2-(4-Aminomethyl-3-phenyl-tetrahydrofuran-2-yloxy)-2-(3,5-bis(trifluoromethyl) phenyl)-ethanol (2SR, 3SR, 4SR, 2[(1')]RS) 2-(3,5-Bis(trifluoromethyl) phenyl)-2-{4-[(N,N-dibenzylamino)methyl]-3-phenyl-tetrahydrofuran-2-yloxy}-ethanol (Description 9(b); 33 mg) was hydrogenated using procedure described in Example 3. Purification was carried out on preparative TLC eluting with 6% methanol in dichloromethane containing 0.2% ammonia to give the title compound (9.2 mg yield 41%).

¹H-NMR (360 MHz, CDCl₃) δ 2.38 (1H, m), 2.82 (1H, dd, J 12.5 Hz, 7.3 Hz), 2.97 (1H, dd, J 12.5 Hz, 7.3 Hz), 3.25(1H, dd, J 6.9 Hz, 2.4 Hz), 3.58 (1H, t, J 8.7 Hz), 3.64–3.70 (2H, m), 4.13 (1H, t, J 8.3 Hz), 5.3 (1H, t, J 5.5 Hz), 5.26 (1H, d, J 2.5 Hz), 7.18–7.38 (5H, m), 7.2 (3H, s).
m/z (ES⁺) 450 (M+H, 3%), 176 (M−273, 100%).

EXAMPLE 5
(2RS)-2-[3,5-Bis(trifluoromethyl)phenyl]-2-({(2SR,3SR, 4SR)-4-[(N,N-dimethylamino)methyl]-3-phenyltetrahydro-2-furanyl}oxy)ethanol (2SR, 3SR, 4SR, 2[(1')]SR) 2-(4-Aminomethyl-3-phenyl-tetrahydrofuran-2-yloxy)-2-(3,5-bis(trifluoromethyl) phenyl)-ethanol ((Example 4; 76 mg) was reductively aminated using the procedure described in Example 2. Purification was carried out by flash silica chromatography eluting with increasing concentrations of methanol (1–4%) in dichloromethane with 0.2% ammonia to give the title compound (50 mg, yield 62%).

¹H-NMR (400 MHz, CDCl₃) δ 2.18 (6H, s), 2.41 (1H, dd, J 11.9 Hz, 5.3 Hz), 2.51 (1H, t, J 9.4 Hz), 2.55–2.67 (1H, m), 3.13 (1H, dd, J 7.7 Hz, 4.4 Hz), 3.65–3.74 (2H, m), 3.97 (1H, t, J 8.8 Hz), 4.37 (1H, dd, J 8.6 Hz, 7.3 Hz), 4.82 (1H, dd, J 7.1 Hz, 3.6 Hz), 5.01 (1H, d, J 3.3 Hz), 7.13–7.32 (5H, m), 7.69 (2H, s), 7.74 (1H, s). m/z (ES⁺) 478 (M+1, 15%), 204 (M−273, 100%).

EXAMPLE 6

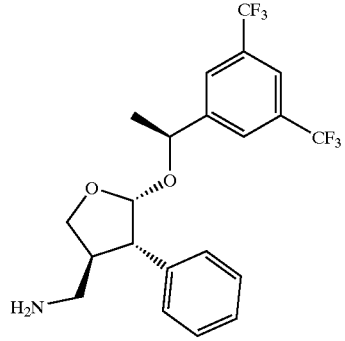

faster eluting
(2RS, 3RS, 4SR, 2[(1')]SR)

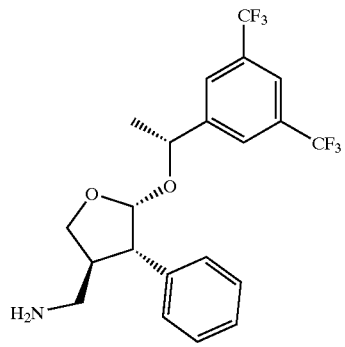

slower eluting
(2RS, 3RS, 4SR, 2[(1')]RS)

(a) [(2RS, 3RS, 4SR)-2-({(1SR)-1-[3,5-Bis(trifluoromethyl) phenyl]-ethyl}oxy)-3-phenyltetrahydro-4-furanyl] methanamine; and (b) [(2RS, 3RS, 4SR)-2-({(1RS)-1-[3,5-Bis(trifluoromethyl)phenyl]-ethyl}oxy)-3-phenyltetrahydro-4-furanyl]methanamine (2RS, 3SR, 4SR) N,N-Dibenzyl-{5-[1-(3,5-bis(trifluoromethyl)phenyl)-vinyloxy]-4-phenyl-tetrahydrofuran-3-ylmethyl}amine (Description 10; 166 mg) was hydrogenated using the procedure described in Example 1. Purification was carried out by flash chromatography elution in increasing concentrations (0–5%) methanol in ethyl acetate with 0.2% ammonia.

Faster eluting isomer (a) (2RS, 3RS, 4SR, 2[(1')]SR) (12 mg, yield 10%).

$^1$H-NMR (360 MHz, CDCl$_3$) δ 1.21 (3H, d, J 6.5 Hz), 2.67 (1H, dd, J 14.1 Hz), 2.84–2.96 (2H, m), 3.05 (1H, dd, J 10.7 Hz, 4.4 Hz), 3.69 (1H, t, J 8.2 Hz), 4.10 (1H, t, J 8.2 Hz), 4.72 (1H, q, J 6.4 Hz), 5.24 (1H, d, J 4.5 Hz), 7.24 (5H, m), 7.72 (2H, s), 7.75 (1H, s). m/z (ES$^+$) 434 (H+1, 20%), 176 (M−273, 100%).

Slower eluting isomer (b) (2RS, 3RS, 4SR, 2[(1')]RS) (30 mg, yield 25%).

$^1$H-NMR (360 MHz, CDCl$_3$) δ 1.40 (3H, d, J 6.6 Hz), 2.70 (1H, dd, J 12.4 Hz), 2.86–3.06 (3H, m), 3.82 (1H, t, J 7.4 Hz), 4.40 (1H, t, J 7.4 Hz), 4.82–4.92 (2H, m), 7.22–7.36 (7H, m), 7.64 (1H, s). m/z (ES$^+$) 434 (H+1, 30%), 176 (M−273, 100%).

EXAMPLE 7

[(2RS, 3RS, 4SR)-5-({(1RS)-1-[3,5-Bis(trifluoromethyl)phenyl]-ethyl}oxy)-3-phenyltetrahydro-4-furanyl]-N,N-diethylmethanamine

[(2RS, 3RS, 4SR)-2-({(1RS)-1-[3,5-Bis(trifluoromethyl)phenyl]ethyl}oxy)-3-phenyltetrahydro-4-furanyl]methanamine (Example 6b; 30 mg) was methylated using the same procedure as described in Example 2. Purification was carried out by preparative TLC eluting with 3.5% methanol in ethyl acetate with 0.2% ammonia to give the title compound (3.6 mg).

$^1$H-NMR (360 MHz, CDCl$_3$) δ 1.39 (3H, d, J 6.6 Hz), 2.25 (6H, s), 2.35–2.40 (2H, m), 2.88 (1H, dd, J 11.2 Hz, 4.6 Hz), 3.06–3.08 (1H, m), 3.85 (1H, t, J 8.3 Hz), 4.43 (1H, t, J 8.3 Hz), 4.84 (1H, q, J 7.6 Hz), 7.24–7.38 (7H,m), 7.64 (1H, s). m/z (ES$^+$) 462 (H+1, 100%).

EXAMPLE 8

(2RS, 3SR, 4SR, 2[(1')]RS) 2-(4-Aminomethyl-3-phenyl-tetrahydrofuran-2-yloxy)-2-(3,5-bis(trifluoromethyl)phenyl)-ethanol (2RS, 3SR, 4SR, 2[(1')]RS) 2-(3,5-Bis(trifluoromethyl)phenyl)-2-{4-[(N,N-dibenzylamino)methyl]-3-phenyl-tetrahydrofuran-2-yloxy}-ethanol (Description 11a; 23 mg) was hydrogenated as described in Example 3. Purification was carried out on preparative TLC eluting with 6% methanol in dichloromethane containing 0.2% ammonia (10.6 mg yield 65%).

$^1$H-NMR (360 MHz, CDCl$_3$) δ 2.70 (1H, dd, J 13.3 Hz, 7.2 Hz), 2.92 (1H, dd, J 13.3 Hz, 5.5 Hz), 2.99–3.06 (1H, m), 3.15 (1H, dd, J 11.7 Hz, 5.5 Hz), 3.40 (1H, dd, J 12.1 Hz, 4.7 Hz), 3.48 (1H, dd, J 12.1 Hz, 4.7 Hz), 3.69 (1H, t, J 8.2 Hz), 4.09 (1H, t, J 8.2 Hz), 4.58 (1H, dd, J 8.2 Hz, 4.7 Hz), 5.24 (1H, d, J 5.5 Hz), 7.30–7.45 (5H, m), 7.74 (2H, s), 7.79 (1H, s). m/z (ES$^+$) 450 (M+H, 3%) 176 (M−273, 100%).

EXAMPLE 9

(2RS, 3SR, 4SR, 2[(1')]SR) 2-(4-Aminomethyl-3-phenyl-tetrahydrofuran-2-yloxy)-2-(3,5-bis(trifluoromethyl)phenyl)-ethanol (2RS, 3SR, 4SR, 2[(1')]SR) 2-(3,5-Bis(trifluoromethyl)phenyl)-2-{4-[(N,N-dibenzylamino)methyl]-3-phenyl-tetrahydrofuran-2-yloxy}-ethanol (Description 11b; 33 mg) was hydrogenated as described in Example 3. Purification was carried out on preparative TLC eluting with 5% methanol in dichloromethane containing 0.2% ammonia (14.9 mg yield 65%).

$^1$H-NMR (360 MHz, CDCl$_3$) δ 2.66–2.79 (1H, m), 2.95–3.17 (3H, m), 3.58 (1H, dd, J 11.8 Hz, 7.5 Hz), 3.68 (1H, dd, J 11.8 Hz, 3.2 Hz), 3.88 (1H, t, J 8.0 Hz), 4.47 (1H, t, J 8.0 Hz), 4.77 (1H, dd, J 7.4 Hz, 3.1 Hz), 5.04 (1H, d, J 4.2 Hz), 7.21–7.37 (7H, m), 7.68 (1H, s). m/z (ES$^+$) 450 (M+H, 3%) 176 (M−273, 100%).

What is claimed is:

1. A compound of the formula (I):

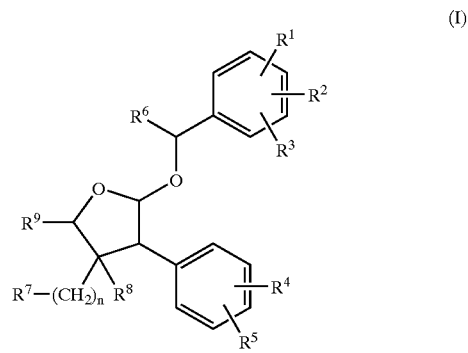

wherein $R^1$ is hydrogen, halogen, $C_{1-6}$alkyl, $C_{1-6}$alkoxy, fluoro$C_{1-6}$ alkyl, fluoro$C_{1-6}$alkoxy, $C_{3-7}$cycloalkyl, $C_{3-7}$cycloalkyl$C_{1-4}$alkyl, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;

$R^2$ is hydrogen, halogen, $C_{1-6}$alkyl, fluoro$C_{1-6}$alkyl or $C_{1-6}$alkoxy substituted by $C_{1-4}$alkoxy;

$R^3$ is hydrogen, halogen or fluoro$C_{1-6}$alkyl;

$R^4$ is hydrogen, halogen, $C_{1-6}$alkyl, $C_{1-6}$alkoxy, fluoro$C_{1-6}$ alkyl, fluoro$C_{1-6}$alkoxy, hydroxy, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, fluoro$C_{1-6}$alkyl or $C_{1-6}$alkoxy substituted by $C_{1-4}$alkoxy;

$R^6$ represents hydrogen or a $C_{1-4}$alkyl group optionally substituted by a hydroxy group;

$R^7$ represents halogen, hydroxy, $C_{2-4}$alkenyl, $C_{2-4}$alkynyl, $N_3$, —$NR^{10}R^{11}$, —$NR^aCOR^b$, —$OSO_2R^a$, —$(CH_2)_p NR^a(CH_2)_q COOR^b$, $COR^a$, $COOR^a$, —N=C=O, or a five membered or six membered nitrogen-containing heteroaromatic ring optionally containing 1, 2 or 3 additional heteroatoms selected from N, O and S which heteroaromatic ring is optionally substituted at any substitutable position by a substituent selected from =O, =S, halogen, hydroxy, —SH, $COR^a$, $CO_2R^a$, -ZNR$^{10}$R$^{11}$, $C_{1-4}$alkyl, hydroxy$C_{1-4}$alkyl, fluoro$C_{1-4}$alkyl, chloro$C_{1-4}$alkyl, $C_{1-4}$alkoxy, fluoro$C_{1-4}$alkoxy or $C_{1-4}$alkoxy substituted by a $C_{1-4}$alkoxy or hydroxyl group, and wherein said $C_{2-4}$alkenyl and $C_{2-4}$alkynyl groups are optionally substituted by a substituent selected from halogen, hydroxy, $N_3$, —$NR^{10}R^{11}$, —$NR^aCOR^b$, —$OSO_2R^a$, —$(CH_2)_p NR^a(CH_2)_q COOR^b$, $COR^a$ or $COOR^a$;

or $R^7$ represents a C-linked nitrogen-containing ring of the formula

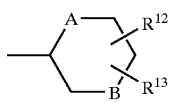

wherein A represents $NR^{14}$ or O, and B represents a bond, $CH_2$, $NR^{14}$ or O, wherein one or both hydrogen atoms in said $CH_2$ moiety may be replaced with one or both of $R^{12}$ and $R^{13}$, or alternatively, one of the hydrogen atoms in said $CH_2$ moiety together with a hydrogen atom from an adjacent carbon are replaced by a double bond;

with the proviso that when A is O, then B is $NR^{14}$;

and with the further proviso that when $R^7$ represents said C-linked nitrogen-containing ring, n is zero and $R^8$ is hydrogen;

$R^8$ represents hydrogen, $C_{1-6}$alkyl, fluoro$C_{1-6}$alkyl, hydroxy, $C_{1-6}$alkoxy or hydroxy$C_{1-6}$alkyl;

$R^9$ represents hydrogen, halogen, $C_{1-6}$alkyl, $CH_2OR^c$, oxo, $CO_2R^a$ or $CONR^aR^b$ where $R^a$ and $R^b$ are as previously defined and $R^c$ represents hydrogen, $C_{1-6}$alkyl or phenyl;

$R^{10}$ is hydrogen, $C_{1-4}$alkyl, $C_{3-7}$cycloalkyl, $C_{3-7}$cycloalkyl$C_{1-4}$alkyl, $C_{2-4}$alkyl substituted by a $C_{1-4}$alkoxy or hydroxyl group, or $R^{10}$ is a five membered or six membered nitrogen-containing heteroaromatic ring as previously defined;

$R^{11}$ is hydrogen or $C_{1-4}$alkyl, $C_{3-7}$cycloalkyl, $C_{3-7}$cycloalkyl$C_{1-4}$alkyl, or $C_{2-4}$alkyl substituted by a $C_{1-4}$alkoxy or hydroxyl group;

or $R^{10}$, $R^{11}$ and the nitrogen atom to which they are attached form a heteroaliphatic ring of 4 to 7 ring atoms, optionally substituted by one or two groups selected from hydroxy, $COR^e$, $CO_2R^e$, $C_{1-4}$alkyl optionally substituted by a $C_{1-4}$alkoxy or hydroxyl group, or $C_{1-4}$alkoxy optionally substituted by a $C_{1-4}$alkoxy or hydroxyl group, or a five membered or six membered nitrogen-containing heteroaromatic ring as previously defined, or said heteroaliphatic ring is substituted by a spiro-fused lactone ring or a spiro-fused ring of the formula —$(CH_2)_rO(CH_2)_s$— (where r and s are each independently zero, 1, 2 or 3 and the sum total of r and s is 3), and said heteroaliphatic ring optionally containing a double bond, which heteroaliphatic ring may optionally contain an oxygen or sulphur ring atom, a group S(O) or $S(O)_2$ or a second nitrogen atom which will be part of a NH or $NR^d$ moiety, where $R^d$ is $C_{1-4}$alkyl optionally substituted by hydroxy or $C_{1-4}$alkoxy, and where $R^e$ is hydrogen, $C_{1-4}$alkyl or benzyl;

or $R^{10}$, $R^{11}$ and the nitrogen atom to which they are attached form a non-aromatic azabicyclic ring system of 6 to 12 ring atoms;

or $R^{10}$, $R^{11}$ and the nitrogen atom to which they are attached form a heteroaliphatic ring of 4 to 7 ring atoms to which is fused a benzene ring or a five membered or six membered nitrogen-containing heteroaromatic ring optionally containing 1, 2 or 3 additional heteroatoms selected from N, O and S;

$R^{12}$ and $R^{13}$ each independently represent hydrogen, hydroxy, $COR^e$, $CO_2R^e$, $C_{1-4}$alkyl optionally substituted by a $C_{1-4}$alkoxy or hydroxyl group, or $C_{1-4}$alkoxy optionally substituted by a $C_{1-4}$alkoxy or hydroxyl group;

or, when they are attached to the same carbon atom, $R^{12}$ and $R^{13}$ may together represent =O, =CHCO_2R^a, —$O(CH_2)_mO$—, —$CH_2O(CH_2)_k$—, —$CH_2OCH_2C(O)$—, —$CH_2OCH_2CH(OH)$—, —$CH_2OCH_2C(CH_3)_2$—, —$CH_2OC(CH_3)_2CH_2$—, —$C(CH_3)_2OCH_2CH_2$—, —$CH_2C(O)OCH_2$—, —$OC(O)CH_2CH_2$—, —$C(O)OCH_2CH_2$—, —$C(O)OC(CH_3)_2CH_2$—, —$C(O)OCH_2C(CH_3)_2$—, —$OCH_2(CH_2)_k$—, —$OC(CH_3)_2CH_2CH_2$—, —$OCH_2C(OCH_3)_2CH_2$—, —$OCH_2CH_2C(CH_3)_2$—, —$OCH_2CH=CHCH_2$—, —$OCH_2CH(OH)CH_2CH_2$—, —$OCH_2CH_2CH(OH)CH_2$—, —$OCH_2C(O)CH_2CH_2$—, —$OCH_2CH_2C(O)CH_2$—, or a group of the formula

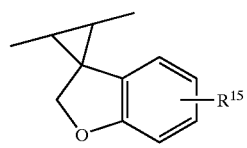

or, where they are attached to adjacent carbon atoms, $R^{12}$ and $R^{13}$ may together represent —$OCH_2CH_2$— or —$OCH_2CH(OH)$—, or $R^{12}$ and $R^{13}$ may together form a fused benzene ring;

or, $R^{12}$ and $R^{13}$ together form a $C_{1-2}$alkylene bridge across the pyrrolidine, piperidine, morpholine or piperazine ring to which they are attached;

$R^{14}$ represents hydrogen, benzyl, $C_{1-4}$alkyl, $C_{3-7}$cycloalkyl, $C_{3-7}$cycloalkyl$C_{1-4}$alkyl, or $C_{2-4}$alkyl substituted by a $C_{1-4}$alkoxy or hydroxyl group;

$R^{15}$ represents hydrogen, halogen, hydroxy, $C_{1-4}$alkyl, hydroxy$C_{1-4}$alkyl or fluoro$C_{1-4}$alkyl;

Z represents a bond, $C_{1-6}$alkylene or $C_{3-6}$cycloalkylene;

k is 1, 2 or 3;

m is 1 or 2;

n is zero, 1 or 2;

p is 1 or 2; and q is 1 or 2;

or a pharmaceutically acceptable salt thereof.

2. A compound as claimed in claim 1 wherein $R^1$ is hydrogen, $C_{1-4}$alkyl, $C_{1-4}$alkoxy, halogen or $CF_3$.

3. A compound as claimed in claim 1 wherein $R^2$ is hydrogen, $C_{1-4}$alkyl, $C_{1-4}$alkoxy, halogen or $CF_3$.

4. A compound as claimed in claim 1 wherein $R^3$ is hydrogen, fluorine, chlorine or $CF_3$.

5. A compound as claimed in claim 1 wherein $R^4$ is hydrogen or fluorine.

6. A compound as claimed in claim 1 wherein $R^5$ is hydrogen, fluorine, chlorine or $CF_3$.

7. A compound as claimed in claim 1 wherein $R^6$ is $C_{1-4}$alkyl optionally substituted by hydroxy.

8. A compound as claimed in claim 1 wherein $R^7$ is $NR^{10}R^{11}$ where the group $NR^{10}R^{11}$ represents a heteroaliphatic ring of 4 to 7 ring atoms substituted by two groups, the first substituent being selected from hydroxy, $CO_2R^e$ (where $R^e$ is hydrogen, methyl, ethyl or benzyl), or $C_{1-2}$alkyl substituted by hydroxy, and the second substituent being a methyl group.

9. The compound of claim 1 wherein $R^8$ is hydrogen or methyl.

10. The compound of claim 1 wherein n is 1 or 2.
11. The compound of claim 1 wherein $R^9$ is hydrogen.
12. The compound of claim 1 of the formula (Ia):

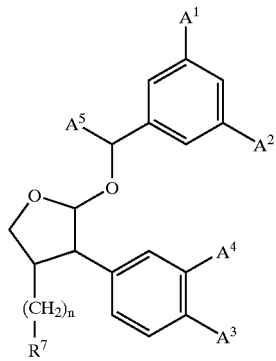

(Ia)

wherein
$A^1$ is fluorine or $CF_3$;
$A^2$ is fluorine or $CF_3$;
$A^3$ is fluorine or hydrogen;
$A^4$ is fluorine or hydrogen; and
$A^5$ is methyl or hydroxymethyl;
or a pharmaceutically acceptable salt thereof.

13. A pharmaceutical composition comprising the compound of claim 1 or a pharmaceutically acceptable salt and a pharmaceutically acceptable carrier or excipient.

14. A method for the treatment of pain or inflammation, migraine, emesis, postherpetic neuralgia, depression or anxiety, which method comprises administration to a patient in need thereof of a therapeutically effective amount of the compound of claim 1 or a pharmaceutically acceptable salt thereof.

* * * * *